United States Patent
Tarinelli

(10) Patent No.: US 7,837,656 B2
(45) Date of Patent: Nov. 23, 2010

(54) DUAL AIR REGULATED SPRAY APPLICATOR

(75) Inventor: Danyel Tarinelli, Middletown, CT (US)

(73) Assignee: Tyco Healthcare Group LP, North Haven, CT (US)

(*) Notice: Subject to any disclaimer, the term of this patent is extended or adjusted under 35 U.S.C. 154(b) by 204 days.

(21) Appl. No.: 11/389,816

(22) Filed: Mar. 27, 2006

(65) Prior Publication Data

US 2007/0225645 A1    Sep. 27, 2007

(51) Int. Cl.
*A61M 5/00* (2006.01)
(52) U.S. Cl. .................. 604/191; 604/121; 128/200.14
(58) Field of Classification Search .................. 604/61, 604/191, 114, 121; 222/71, 135, 145.5; 128/200.14
See application file for complete search history.

(56) References Cited

U.S. PATENT DOCUMENTS

| | | | | |
|---|---|---|---|---|
| 4,261,481 A | * | 4/1981 | Speer | 222/135 |
| 4,631,055 A | * | 12/1986 | Redl et al. | 604/82 |
| 5,605,541 A | * | 2/1997 | Holm | 604/82 |
| 6,132,396 A | * | 10/2000 | Antanavich et al. | 604/82 |
| 6,461,325 B1 | * | 10/2002 | Delmotte et al. | 604/82 |
| 6,796,964 B2 | * | 9/2004 | Eidson et al. | 604/135 |
| 6,860,870 B2 | | 3/2005 | Pichon et al. | |
| 2003/0225380 A1 | | 12/2003 | Redl et al. | |
| 2004/0050867 A1 | * | 3/2004 | Alexander et al. | 222/145.5 |
| 2004/0059283 A1 | * | 3/2004 | Kirwan et al. | 604/23 |
| 2004/0159715 A1 | * | 8/2004 | Leach | 239/1 |

OTHER PUBLICATIONS

International Search Report (PCT/US07/07614 dated Feb. 22, 2008).
PCT International Search Report for U.S. PCT Patent Application No. PCT/US07/07614 dated Mar. 27, 2007 (2 pages).

* cited by examiner

*Primary Examiner*—Kevin C Sirmons
*Assistant Examiner*—Deanna K Hall

(57) ABSTRACT

An applicator device 6 is provided to mix and apply two or more compositions of adhesive or sealant to tissue or bone. The applicator device generally includes an applicator assembly having a handle containing a double-barreled syringe, removably mounted thereto, and a regulator assembly for providing control and sources of air pressure to the applicator assembly.

19 Claims, 7 Drawing Sheets

DUAL AIR REGULATED SPRAY APPLICATOR

BACKGROUND

1. Technical Field

The present disclosure relates to a dual air regulated spray applicator. More particularly, the present disclosure relates to an applicator device having a double-barreled syringe or cartridge, removably mounted on a handle, and containing components or compositions of a tissue adhesive or sealant, e.g., glue, tissue sealant or bone cement, to be mixed by an applicator assembly of the device.

2. Background of Related Art

During various surgical procedures it is often necessary to close puncture wounds, leaks or incisions in tissue. Typically, this is done through the use of sutures or staples to close the puncture wounds, leaks or incisions. Recently however, various synthetic and/or natural adhesive or sealant substances have been developed to be applied to tissue. Originally, the compositions of the adhesives or sealants were simply mixed together and applied with an applicator device or stick. Advancements in this technology have provided devices which are capable of receiving the compositions from external sources and expelling them onto tissue to be mixed on the tissue site. These devices are often cumbersome and bulky and provide little or no control over the amount of pressure used to discharge the various compositions and/or compensate for the appropriate mixture percentages.

Therefore, it may be desirable to provide a self-contained applicator device having a cartridge or double-barreled syringe, containing the separate components or compositions to be mixed into an adhesive or sealant, removably mounted to a handle. It may also be desirable to have a self-contained applicator device capable of mixing the compositions within the device and expelling them as a single composition of an adhesive or sealant for application to tissue. It may be further desirable to have an applicator device capable of varying the amounts of pressure to each of the compositions in order to adjust for the mixtures of the components contained therein.

SUMMARY

The present disclosure relates to a dual air regulated spray applicator. The dual air regulated spray applicator includes an applicator assembly having a handle and a double-barreled syringe removably mounted to the handle. The dual air regulated spray applicator also includes a regulator assembly connected to the applicator assembly for providing a source of pressure to the applicator assembly. An atomizing tip is provided at a distal end of the handle and is in fluid communication with the double-barreled syringe to mix the components contained therein. In the disclosed embodiment, the atomizing tip is configured to mix a first and a second composition received from the double-barreled syringe. In alternative embodiments, the syringe used with the handle may contain more than two chambers or cylinders for mixing more than two compositions.

In a disclosed embodiment, the double-barreled syringe includes a first and a second cylinder. Each cylinder includes a pressure intake port at a proximal end and a fluid discharge port at a distal end of the cylinder. The first and second cylinders made be provided separately or joined as a single unit. Each of the cylinders includes a plunger movably mounted within the cylinder which moves distally in response to air pressure provided at the pressure intake port to force compositions contained within the cylinder toward, and out of the fluid discharge port. The atomizing tip is in fluid communication with the fluid discharge ports of the first and second cylinders. A pair of clips is provided on the handle to retain the first and second cylinders within the handle.

The regulator assembly includes a first regulator which provides a source of air pressure to the first cylinder and a second regulator which provides a source of air pressure to the second cylinder. Flow control knobs are provided on the first and second regulators which vary the amount of air pressure discharged therefrom. Additionally, the regulators may be provided with a failsafe mechanism which turns off air pressure from all regulators in the event the air pressure sensed by any regulator exceeds a predetermined amount.

The regulator assembly may additionally include a third regulator to provide a source of atomizing air pressure to the atomizing tip to mix the compositions discharged from the first and second cylinders. The disclosed atomizing tip has a single fluid discharge port to discharge the mixed composition, e.g., tissue sealant, adhesive, bone cement, etc.

An embodiment of the disclosed applicator device includes an actuator assembly. The actuator assembly includes a controller associated with the regulator assembly that controls the flow of pressure out of the regulator assembly and also includes an actuator associated with the handle to operate the controller. In a disclosed embodiment, the actuator is a contact switch disposed within the handle and a trigger is pivotally mounted to the handle to actuate the contact switch.

In a disclosed embodiment, the applicator device comprises a static mixer disposed at least partially within the atomizing tip.

DESCRIPTION OF THE DRAWINGS

An embodiment of the presently disclosed dual air regulated spray applicator is disclosed herein with reference to the drawings, wherein.

DETAILED DESCRIPTION OF EMBODIMENTS

An embodiment of the presently disclosed dual air regulated spray applicator is described in detail with reference to the drawings wherein like numerals designate identical or corresponding elements in each of the several views. As is common in the art, the term "proximal" refers to that part or component closer to the user or operator, e.g., surgeon or physician, while the term "distal" refers to that part or component farther away from the user.

Figure 1:
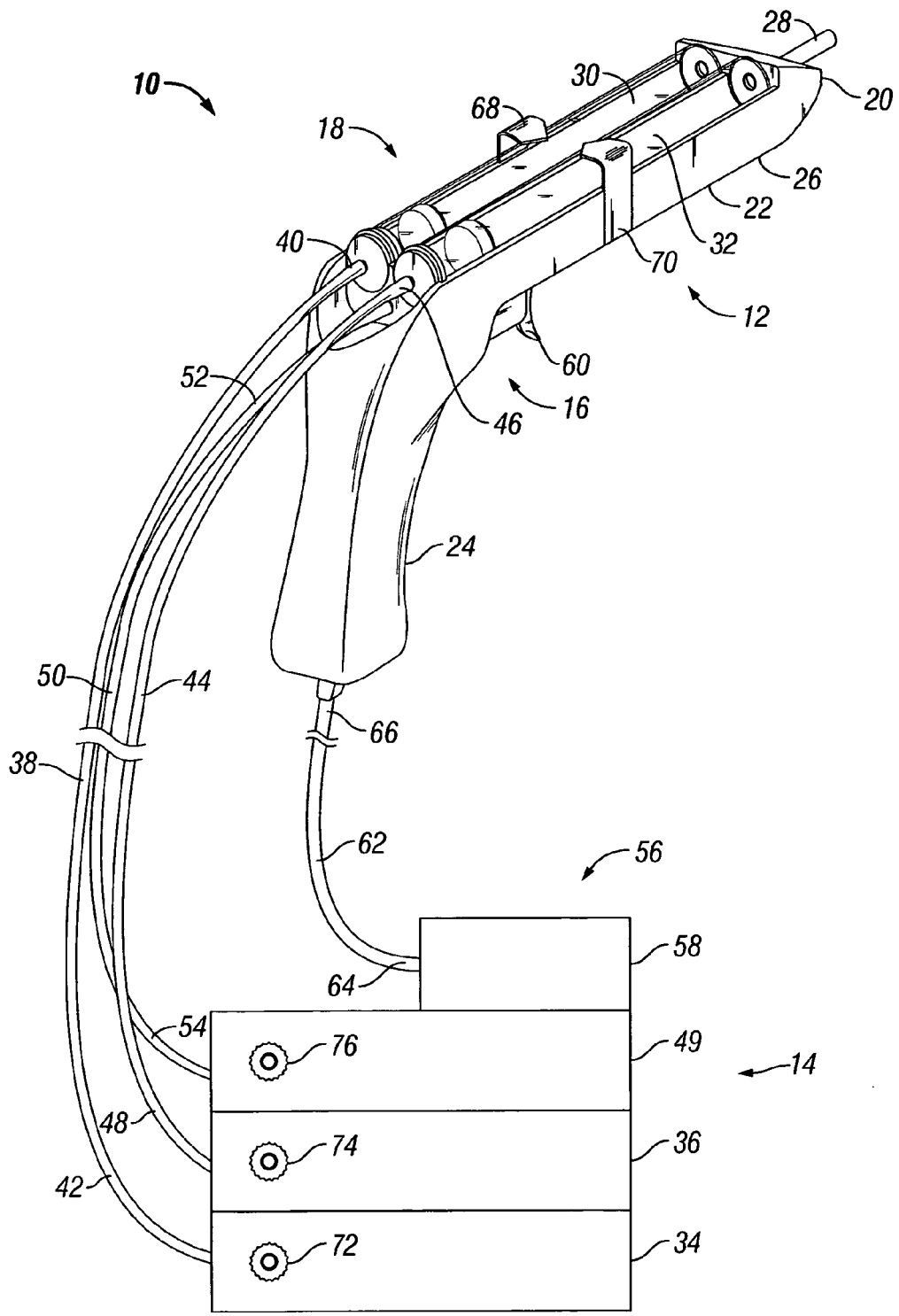
FIG. 1 is a perspective view an applicator assembly in accordance with an embodiment of the present disclosure.

FIG. 1 illustrates one embodiment of the presently disclosed dual air regulated spray applicator or applicator device 10 which generally includes an applicator assembly 12 and a regulator assembly 14. Applicator assembly 12 includes a handle 16 and a double-barreled syringe 18 removably mounted within handle 16. An atomizing tip 20 is provided to mix the compositions contained within both parts of the double-barreled syringe 18. As used herein, the terms composition and component are used interchangeably. Specifically, handle 16 includes an elongate portion 22 and a pistol grip 24 depending from elongate portion 22. As shown, atomizing tip 20 is provided at a distal end 26 of elongate portion 22. Atomizing tip 20 may be formed as an integral part of elongate portion 22 or as a separate component. A single discharge tube 28 is provided on or adjacent atomizing tip 20 to apply the mixed compositions to tissue.

Double-barreled syringe 18 includes a first cylinder 30 and a second cylinder 32. First and second cylinders 30 and 32, respectively, are provided to contain first and second components of a two-part mixture. First and second cylinders 30 and 32, respectively, may be provided as individual components or may be supplied joined together as a single cartridge type unit. First cylinder 30 and second cylinder 32 may be formed of any suitable material such as, for example, stainless steel, glass, polymers, etc. When formed of a glass or polymeric material, either or both of first cylinder 30 and second cylinder 32 may be transparent or translucent so as to visibly determine the amount of composition remaining within first cylinder 30 and/or second cylinder 32. As noted above, double-barreled syringe 18 is mounted in handle 16. More specifically, double-barreled syringe 18 is mounted in elongate portion 22 handle 16.

Regulator assembly 14 generally includes a first regulator 34 for providing a source of air pressure to first cylinder 30 and a second regulator 36 for providing a source of air pressure to second cylinder 32. First and second regulators 34 and 36, respectively, may be adjusted to provide equal air pressure to both first and second cylinders 30 and 32 or may supply differing levels of air pressure to first and second cylinders 30 and 32 depending upon the percentage mixture of the compositions contained within cylinders 30 and 32. A first pressure line 38 is connected at its distal end 40 to first cylinder 30 and at its proximal end 42 to first regulator 34. Similarly, a second pressure line 44 is connected at its distal end 46 to second cylinder 32 and at its proximal end 48 to second regulator 36. First and second pressure lines 38 and 44 conduct air pressure from first and second regulators 34 and 36, to first and second cylinders 30 and 32, respectively.

A third regulator 49 is provided to supply a source of air pressure to atomizing tip 20. A third pressure line 50 is provided between third regulator 49 and handle 16. A distal end 52 of third pressure line 50 is connected through pistol grip 24 and a proximal end 54 of third pressure line 50 is connected to third regulator 49.

Applicator device 10 also includes an actuator assembly 56 to start and stop the flow of air pressure from regulator assembly 14 to applicator assembly 12. Actuator assembly 56 includes a controller 58 operatively associated with regulator assembly 14 and a trigger 60 mounted on pistol grip 24. A control cable 62 is connected at its proximal end 64 to controller 58 and at its distal end 66 to pistol grip 24. Depression of trigger 60 causes controller 58 to operate regulator assembly 14 in a manner described in more detail herein below.

As shown, handle 16 includes a first clip 68 and a second clip 70 to retain first and second cylinders 30, 32, respectively, within elongate portion 22 of handle 16.

The level of pressure provided by first regulator 34, second regulator 36, and third regulator 49 may be manually adjusted to the same or differing pressure levels. A first adjustment or flow control knob 72 is provided on first regulator 34 and a second adjustment or flow control knob 74 is provided on second regulator 36 to adjust the pressure levels. Similarly, a third adjustment or flow control knob 76 is provided on third regulator 49 to adjust the pressure to atomizing tip 20. Notably, the air pressure flowing through third regulator 49 may be set at a first level during operation to facilitate mixing the first and second components within atomizing tip 20. Further, the pressure level provided by third regulator 49 may be set at a second level when first regulator 34 and second regulator 36 are turned off, or in the absence of double-barreled syringe 18, to facilitate cleaning or clearing any residual components contained within atomizing tip 20 or discharge tube 28.

Figure 2:
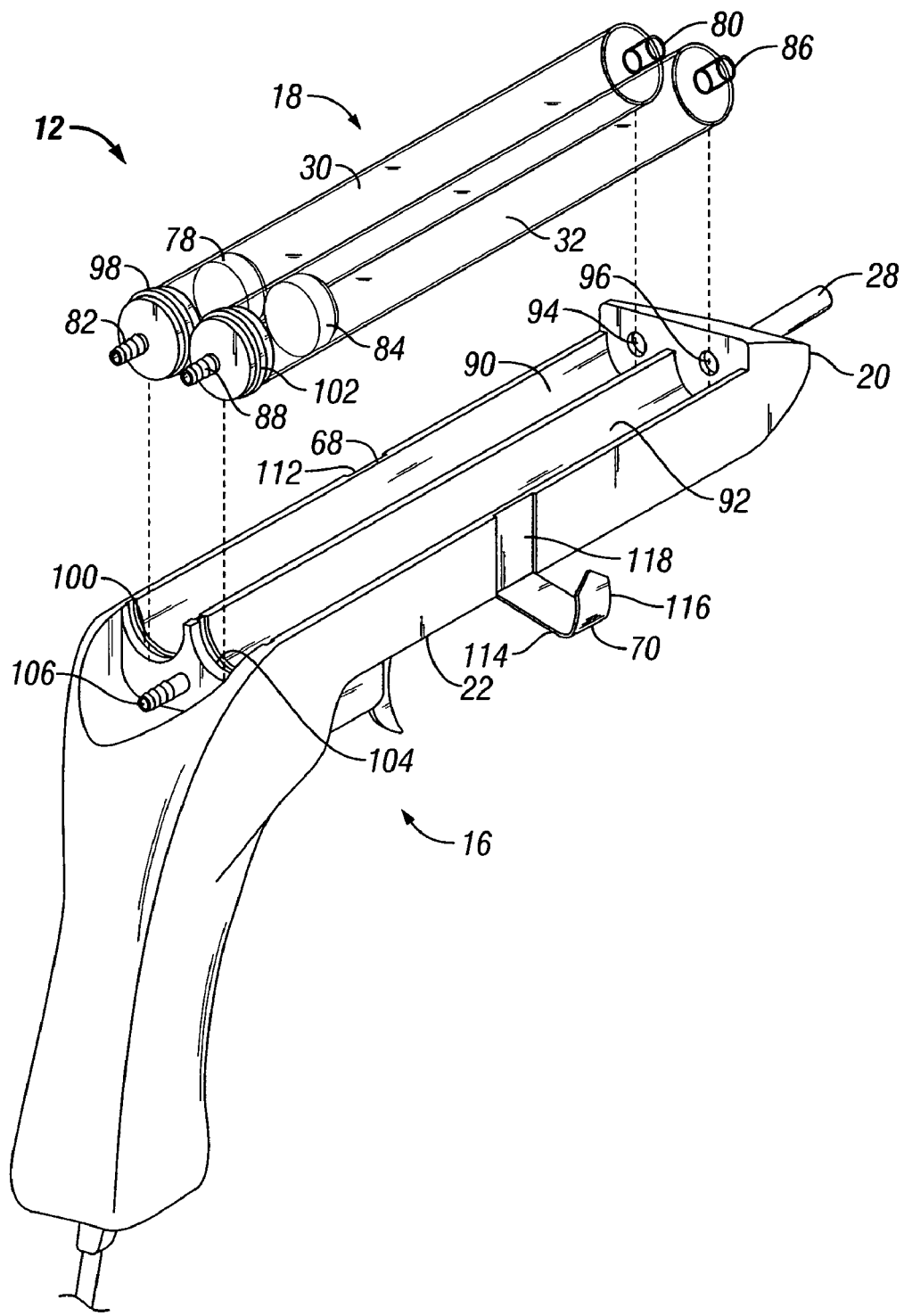
FIG. 2 is a perspective view of an applicator assembly of the FIG. 1 with a double barreled syringe separated from a pistol grip handle.

Referring now to FIG. 2, as noted above, double-barreled syringe 18 includes a first cylinder 30 and a second cylinder 32. A first plunger 78 is movably mounted within first cylinder 32 and is provided to eject a first composition out of first cylinder 32 and into atomizing tip 20. First cylinder 32 includes a first discharge tube 80 which is in fluid communication with atomizing tip 20. First cylinder 30 also includes a first pressure inlet 82 for connection to distal end 40 of first pressure line 38. Likewise, second cylinder 32 includes a second plunger 84 movably mounted therein to eject a second composition into atomizing tip 20. Second cylinder 32 also includes a second discharge tube 86 in fluid communication with atomizing tip 20 and a second pressure inlet 88 for connection to distal end 46 of second pressure line 44. As shown, first pressure inlet 82 and second pressure inlet 88 are ribbed to secure first pressure line 38 and second pressure line 44 thereto. It is also envisioned for at least one of first pressure inlet 82 and second pressure inlet 88 to be threaded.

With continued reference to FIG. 2, double-barreled syringe 18 is removably mounted within handle 16. Elongated portion 22 of handle 16 is provided with a first channel 90 for receipt of first cylinder 30 and a second channel 92 for receipt of second cylinder 32. A first atomizing port 94 is provided on atomizing tip 20 for receipt of first discharge tube 80. A second atomizing port 96 is provided on atomizing tip 20 for receipt of second discharge tube 86.

To secure double-barreled syringe 18 against longitudinal motion within handle 16, a first circumferential projection 98 is provided on first cylinder 30 and is engageable with a first recess 100 on handle 16. Likewise, a second circumferential projection 102 is provided on second cylinder 30 and is engageable with a second recess 104 on handle 16. Other suitable methods may be used to secure double-barreled syringe 18 within handle 16.

A third pressure inlet port 106 is provided on handle 16 for connection to distal end 52 of third pressure line 50. Third pressure inlet port 106 is in fluid communication with atomizing tip 20 in a manner described in more detail herein below.

Figure 3:
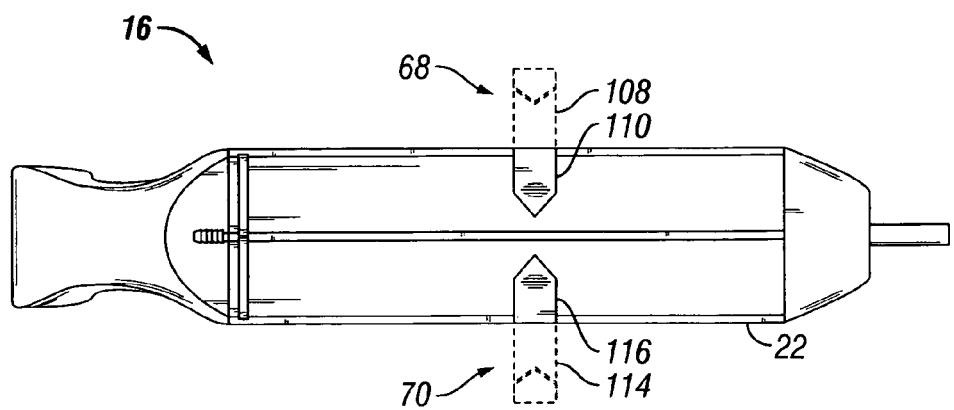
FIG. 3 is a top view of the applicator assembly of FIGS. 1 and 2.
Figure 4:
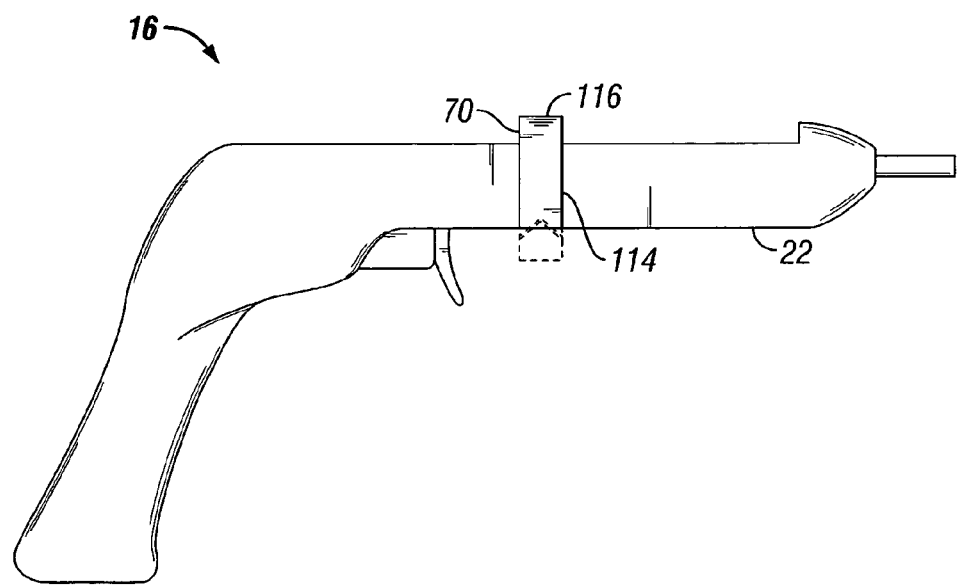
FIG. 4 is a side view of the applicator assembly of FIGS. 1-3.

Referring now to FIGS. 2, 3 and 4, the operation of first clip 68 and second clip 70 to retain double-barreled syringe 18 within elongate portion 22 of handle 16 is described. As shown, first clip 68 includes a straight portion 108 and an angled portion 110. First clip 68 is pivotally mounted to elongate portion 22 and is movable from an open position wherein straight portion 108 is spaced from a first recess 112 formed in elongate portion 22 to a closed position wherein straight portion 108 is substantially flush within first recess 112. In the closed position, angled portion 110 secures cylinder 30 within first channel 90 formed in handle 16. Likewise, second clip 70 is pivotally mounted to elongate portion 22 and is movable from an open position wherein straight portion 114 is spaced from a second recess 118 to a closed position wherein straight portion 114 is substantially flush within second recess 118. In the closed position, angled portion 116 secures second cylinder 32 within recess 92 formed in handle 16. As noted above, cylinders 30 and 32 of double-barreled syringe 18 may be provided as a single unit or maybe provided separately.

Figure 5A:
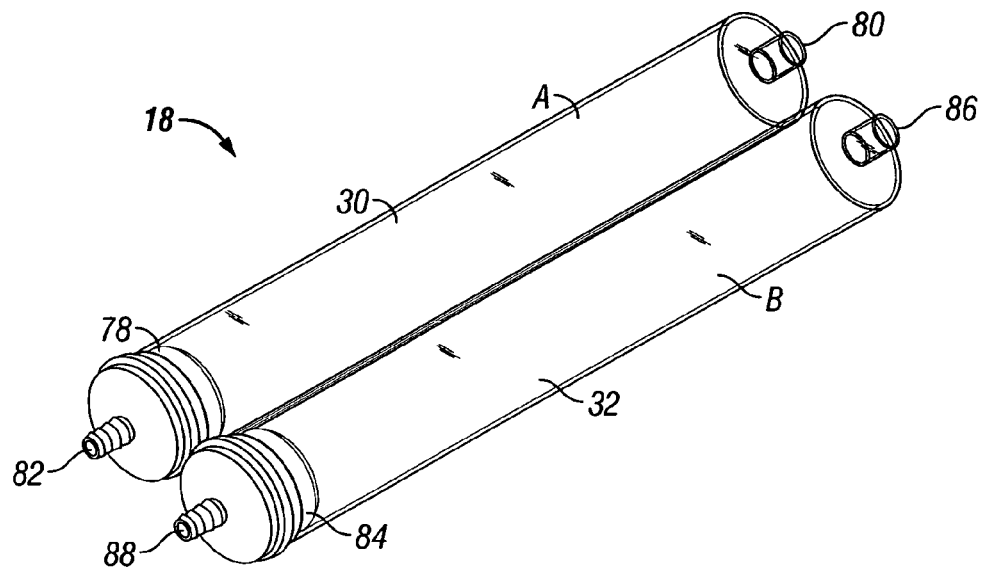
FIG. 5A is a perspective view of the double-barreled syringe of the applicator assembly of FIGS. 1-4.
Figure 5B:
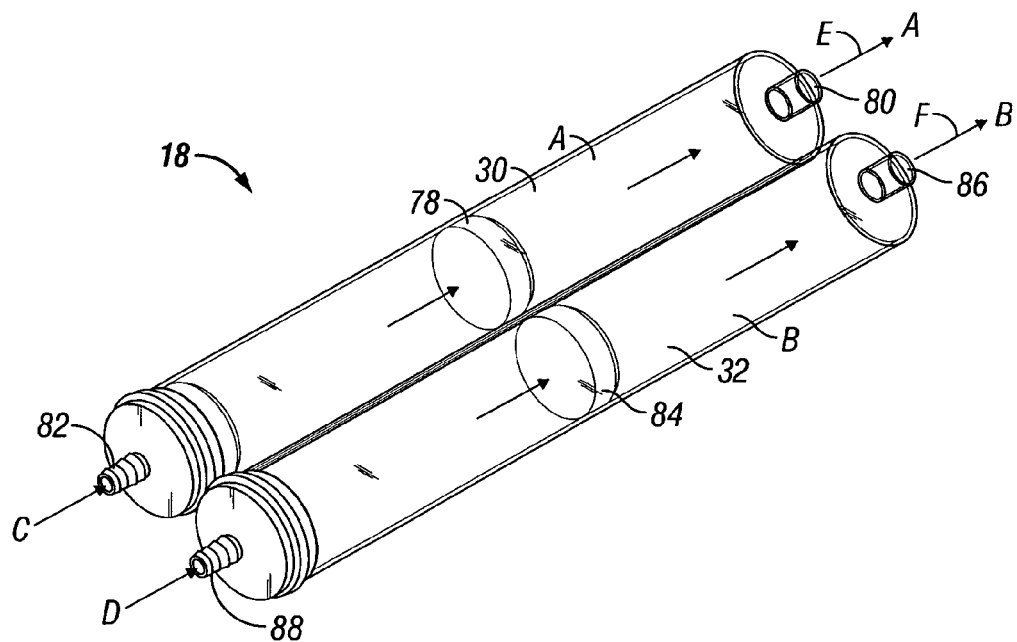
FIG. 5B is a perspective view of the double-barreled syringe of the applicator assembly of FIGS. 1-5A, during operation.

Referring to FIGS. 5A and 5B, the operation of first plunger 78 and second plunger 84 is described. As shown in FIG. 5A, in an initial position, first plunger 78 and second plunger 84 are in a proximal-most position within first cylinder 30 and second cylinder 32, respectively. First composition A is contained within first cylinder 30 and second composition B is contained within second cylinder 32.

Referring now to FIG. 5B, as air pressure is injected into first pressure inlet 82, in the direction of arrow C, the air pressure drives first plunger 78 distally within first cylinder 30. As first plunger 78 moves distally, it forces first composition A distally and out first discharge tube 80 in the direction of arrow E. Likewise, as air pressure is injected into second pressure inlet 88, in the direction of arrow D, the air pressure drives second plunger 84 distally within second cylinder 32 to force second composition B out of second discharge tube 86 and in the direction of arrow F. As noted above, first discharge tube 80 and second discharge tube 86 are in fluid communication with atomizing tip 20. Thus, first and second compositions A and B are forced into atomizing tip 20 to be mixed therein.

Figure 7A:
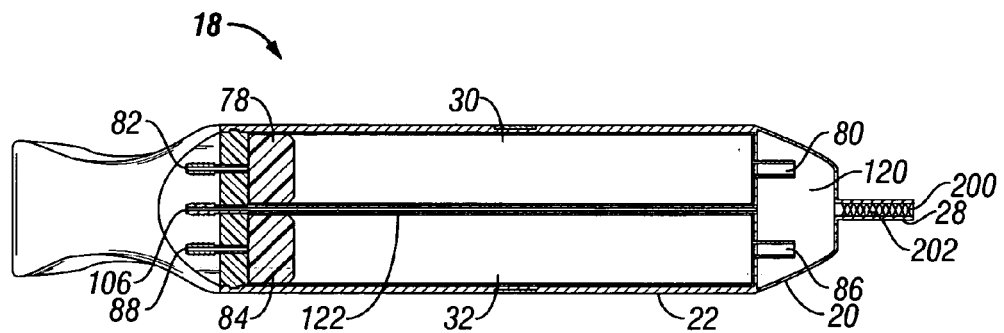
FIG. 7A is a top view of the applicator assembly of FIGS. 1-6, partially shown in section and prior to actuation.

As illustrated in FIG. 7A, it is envisioned for a portion of the atomizing tip 20 to include a static mixer 200. For instance, static mixer 200 may be disposed at least partially within discharge tube 28 and/or within an atomizing chamber 120 (discussed below). Further, static mixer 200 may include a plurality of baffles 202 or the like. In this embodiment, as first and second compositions A and B are forced through static mixer 200, compositions A and B may be repeatedly divided by baffles 202 and recombined, creating a substantially uniform mixture. Baffles 202 of this embodiment may remain substantially motionless as first and second compositions A and B pass therethrough. The mixture may then be discharged toward a target site.

The operation of applicator device 10 to mix and atomize first and second components, or first and second compositions A and B, and discharge them from applicator device 10 is described. Prior to assembling double-barreled syringe 18 with handle 16, the appropriate double-barreled syringe 18, having cylinders 30 and 32 containing the desired compositions A and B is selected, depending upon the intended use. Referring to FIGS. 1 and 2, double-barreled syringe 18 is inserted into handle 16 by initially positioning first discharge tube 80 within first atomization port 94 and second discharge tube 86 within second atomization port 96. First circumferential projection 98 is positioned within first recess 100 and second circumferential projection 102 is positioned within second recess 104. As noted above, first and second cylinders 30 and 32 are received within first channel 90 and second channel 92 formed in elongate portion 22 of handle 16. Thereafter, double-barreled syringe 18 is secured to handle 16 by pivoting first clip 68 and second clip 70 about cylinders 30 and 32, respectively.

Referring to FIGS. 1 and 2, distal end 40 of first pressure line 38 is positioned over first pressure inlet 82 on first cylinder 30. Likewise, distal end 46 of second pressure line 44 is positioned over second pressure inlet 88 on second cylinder 32. Distal end 52 of third pressure line 50 is positioned over third pressure inlet 106. Applicator device 10 may be provided with control cable 62 permanently affixed to controller 58 or may be detachable therefrom.

Referring to FIG. 7A, atomizing tip 20 includes atomizing chamber 120 in fluid communication with discharge tube 28. As shown, first and second discharge tubes 80 and 86 of cylinders 30 and 32, respectively, are in fluid communication with atomizing chamber 120. As noted hereinabove, third pressure inlet 106 is in fluid communication with atomization tip 20 and thus with atomizing chamber 120. A pressure bore 122 extends from third pressure inlet 106 to atomizing chamber 120. Thus, air pressure forced through third pressure inlet 106 is directed into atomizing chamber 120 to facilitate mixing and atomization of compositions A and B discharged from first and second discharge tubes 80 and 86, respectively. As an alternative to atomizing chamber 120, discharge tubes 80 and 86 may be directly connected to discharge tube 28 to mix the compositions within discharge tube 28. In this embodiment, pressure bore 122 will also be in direct fluid communication with discharge tube 28 to mix the compositions therein and provide a source of discharge air pressure.

Figure 8A:
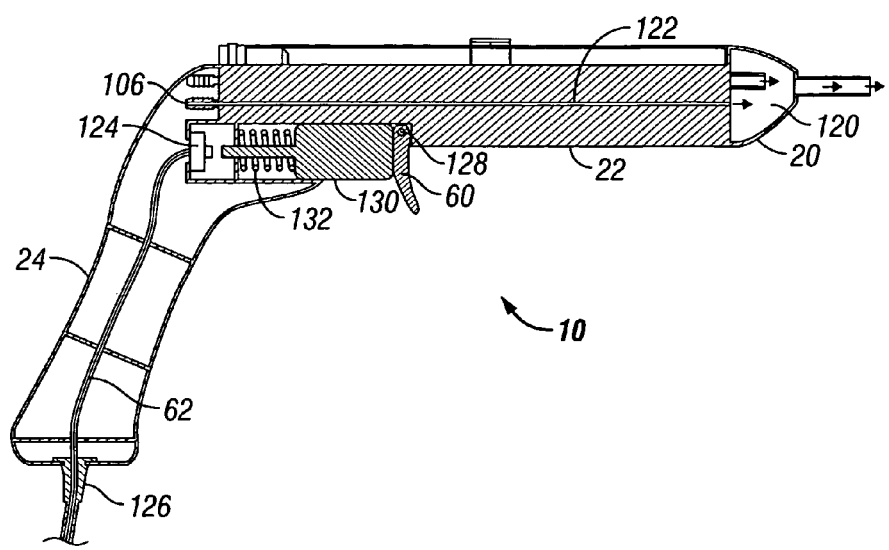
FIG. 8A is a side view of the applicator assembly of FIGS. 1-7, partially shown in section and prior to actuation.

With reference to FIG. 8A, further components of actuation assembly 56 are described. A contact switch 124 is positioned within pistol grip 24 and is connected to control cable 62. Control cable 62 enters pistol grip 24 and is supported within pistol grip 24 by a grommet 126. Trigger 60 is pivotally mounted to elongate portion 22 at a pivot point 128. Trigger 60 is pivotable to engage and move a depressor 130 against contact switch 124 to actuate applicator device 10. Depressor 130 is biased away from contact switch 124 by a spring 132.

Figure 6:
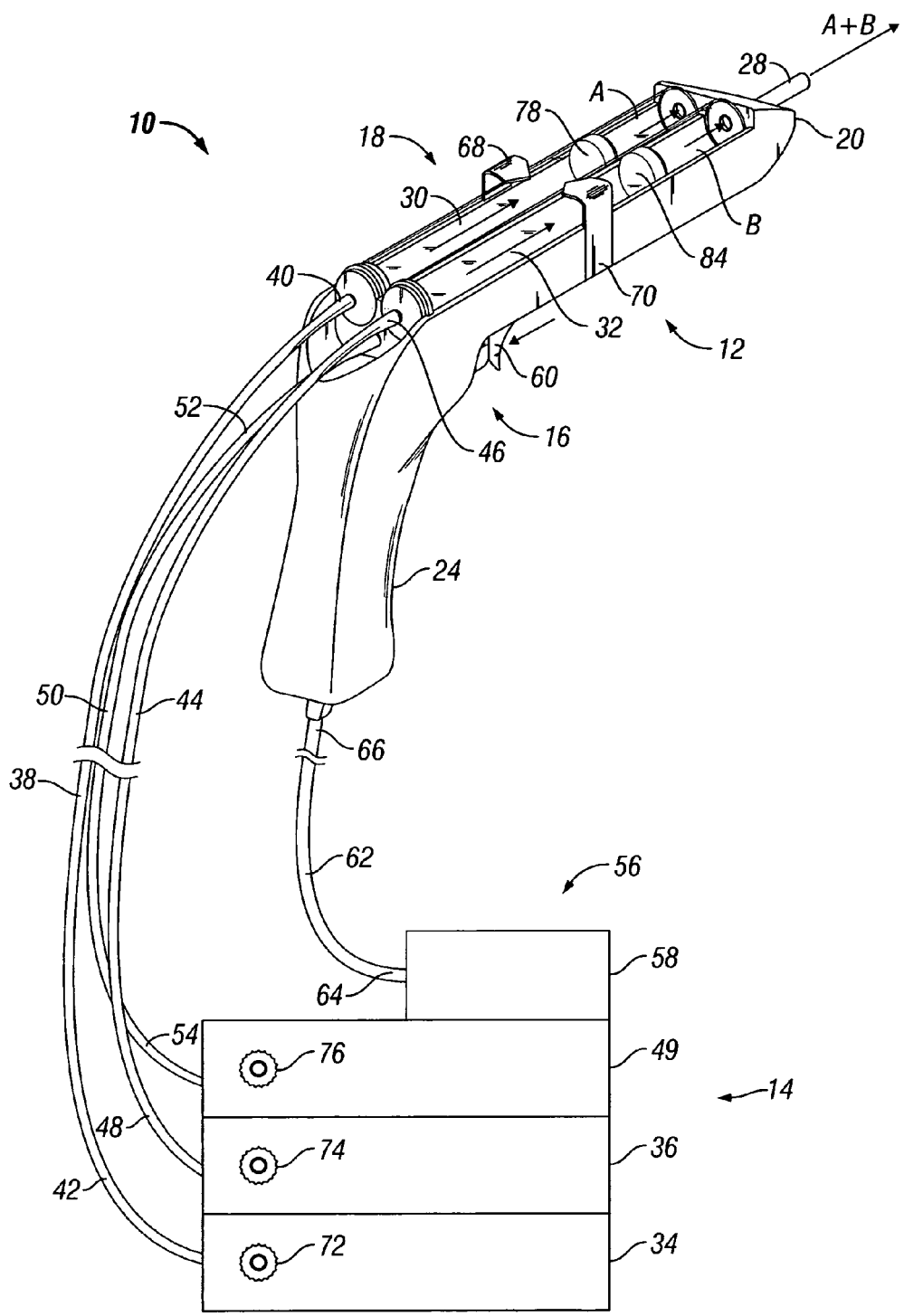
FIG. 6 is a perspective view of the applicator assembly of FIGS. 1-5, during operation.
Figure 7B:
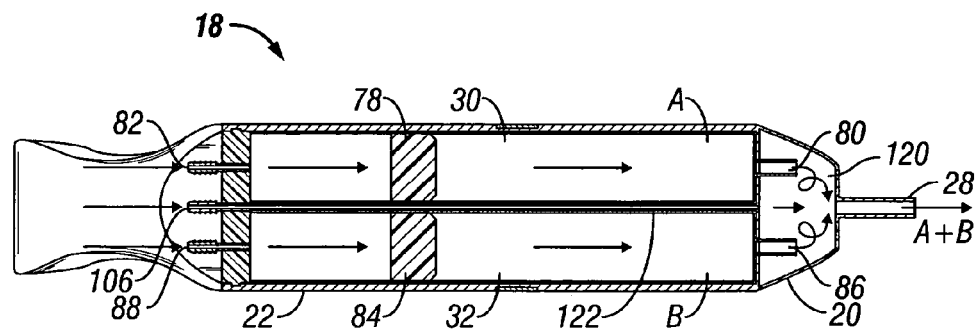
FIG. 7B is a top view of the applicator assembly of FIGS. 1-7A, partially shown in section and during actuation.
Figure 8B:
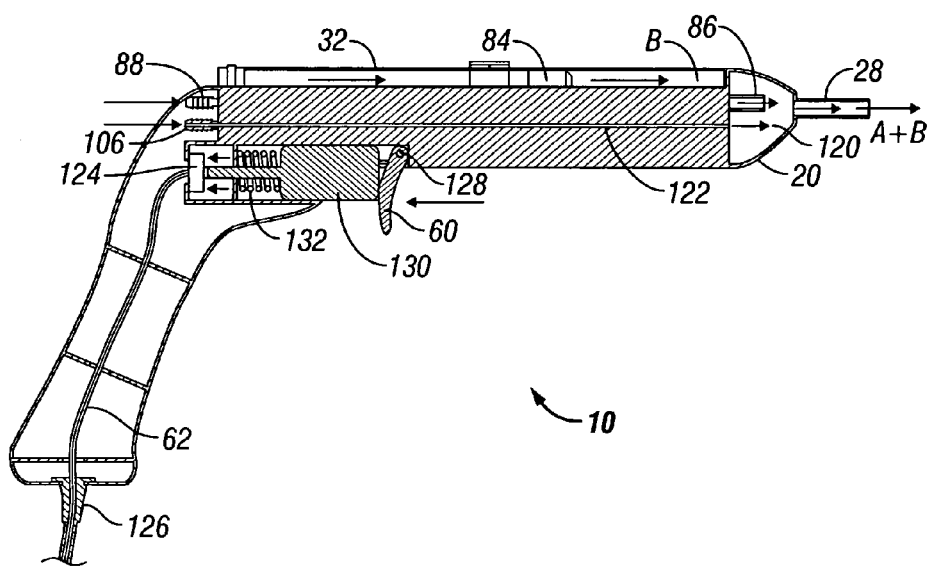
FIG. 8B is a side view of the applicator assembly of FIGS. 1-8A, partially shown in section and during actuation.

Referring now to FIGS. 6, 7B and 8B, to actuate applicator device 10 regulator flow control knobs 76, 74, and 72 are set to the appropriate levels. Trigger 60 is depressed against the bias of spring 132 moving depressor 130 into engagement with contact switch 124. This actuates controller 58 which in turn actuates first regulator 34 providing a first source of air pressure source through pressure line 38 to first cylinder 30 and actuates second regulator 36 which provides a second source of air pressure through pressure line 44 to second cylinder 32. Air pressure in cylinders 30 and 32 drives plungers 78 and 84 distally forcing first composition A and second composition B towards their respective discharge tubes 80 and 86. Thus, first composition A and second composition B are forced into atomizing chamber 120 of atomization tip 20.

As trigger 60 is depressed, it also actuates third regulator 49 which causes a flow of air pressure through pressure line 50 and pressure bore 122 in elongate portion 22 and into atomizing chamber 120. As air pressure is forced into atomizing chamber 120, the air pressure mixes, or atomizes, compositions A and B together to form a single composition A+B which is discharged out of applicator device 10 through discharge tube 28 for application to tissue or bone.

Once the operator has finished using applicator device 10 to apply be substances, e.g., tissue adhesive or sealant, bone cement, etc., trigger 60 is released, thus discontinuing actuation of the applicator device. Thereafter, clips 68 and 70 can be pivoted away from elongate portion 22 to remove double-barreled syringe 18. Should further use of applicator device 10 be necessary, trigger 60 can again be depressed causing a flow of air from third regulator 49 into atomizing chamber 120 and discharge tube 28 to clear any residual compositions contained therein. A subsequent double-barreled syringe 18 containing further or different compositions may be installed in handle 16 and the procedure repeated.

It is envisioned that atomizing tip 20 or another suitable part of applicator device 10 is disposable. It is further envisioned that atomizing ports 94, 96 are disposed in a removable insert (not shown), which is insertable near distal end 26 of the elongate portion 22. The insert may also be disposable.

It will be understood that various modifications may be made to the embodiments disclosed herein. For example, while the disclosed applicator device uses a double-barreled syringe for mixing two compositions, it is also contemplated that multiple barreled syringes along with additional regulators may be provided to mix more than two compositions through the applicator device. Further, as noted above, as an alternative to the use of an atomizing chamber, the discharge tubes of the cylinders may be directed directly into the discharge tube of the atomization tip and the third source of air pressure directed directly into the discharge tube of the atomization tip to mix the compositions directly within the discharge tube. Additionally, while the applicator assembly and regulator assembly have been described as separate units connected by pressure and control lines, the regulator assembly, including the controller, may be contained entirely within the applicator assembly for a single compact unit. Still further, other sources of driving fluid or gas, such as, for example, saline, oil, etc., or combinations thereof, may be used as an alternative to or in combination with air as a source of the driving pressure. Therefore, the above description should not be construed as limiting, but merely as exemplifications of particular embodiments. Those skilled in the art will envision other modifications within the scope and spirit of the claims appended hereto.

The invention claimed is:

1. An applicator device for use in surgical procedures comprising:
    an applicator assembly having a handle and a double-barreled syringe removably mounted to the handle, wherein the double-barreled syringe includes a first cylinder and a second cylinder, each cylinder including a respective pressure intake port at a proximal end and a fluid discharge port at a distal end;
    a regulator assembly connected to the applicator assembly for providing a source of pressure to the applicator assembly; and
    an atomizing tip provided at a distal end of the handle wherein the atomizing tip is in fluid communication with the double-barreled syringe, the atomizing tip including a proximal end defining a substantially hollow chamber configured to receive and mix a first and a second composition from the double-barreled syringe, and a distal end configured to apply a mixture of the first and second compositions to tissue,
    wherein the regulator assembly includes first and second regulators in fluid communication with the respective pressure intake ports associated with each of the cylinders and a third regulator in fluid communication with a pressure intake port disposed on the applicator, each of the first, second, and third regulators is independently controllable from one another and configured to provide a distinct amount of pressurized gas to its respective intake ports.

2. The applicator device as recited in claim 1, wherein the proximal end of the atomizing tip is in fluid communication with the pressure intake port disposed on the handle via a pressure bore configured to provide a passageway for an atomizing pressure to facilitate mixing of the first and second compositions within the proximal end of the atomizing tip.

3. The applicator device as recited in claim 1, wherein the first cylinder and the second cylinder are at least partially separated from one another.

4. The applicator device as recited in claim 1, wherein the first cylinder and the second cylinder are joined together.

5. The applicator device as recited in claim 1, wherein each of the first cylinder and the second cylinder includes a plunger movably mounted therewithin.

6. The applicator device as recited in claim 1, wherein the handle includes a pair of clips, each clip to retain one of the first cylinder and the second cylinder within the handle.

7. The applicator device as recited in claim 1, wherein the atomizing tip is in fluid communication with the fluid discharge ports on the first cylinder and the second cylinder.

8. The applicator device as recited in claim 1, wherein the first regulator and the second regulator each include a failsafe mechanism configured to shut off the sources of pressure to the first cylinder and the second cylinder when the pressure in either of the first cylinder and the second cylinder exceeds a predetermined level.

9. The applicator device as recited in claim 1, wherein at least one of the first regulator and the second regulator is adjustable to vary the amount of pressure discharged therefrom.

10. The applicator device as recited in claim 1, wherein the third regulator provides a source of atomizing pressure to the atomizing tip formed on a distal end of the handle to mix a first composition and a second composition contained within the double-barreled syringe.

11. The applicator device as recited in claim 1, wherein the atomizing tip has a single fluid discharge port.

12. The applicator device as recited in claim 1, further comprising an actuator assembly having a controller associated with the regulator assembly to control the flow of pressure out of the regulator assembly and an actuator associated with the handle to operate the controller.

13. The applicator device as recited in claim 12, wherein the actuator includes a trigger mounted on the handle and a contact switch.

14. The applicator device as recited in claim 1, further comprising a static mixer disposed at least partially within the atomizing tip.

15. An applicator device for use in surgical procedures comprising:
    an applicator assembly having a handle and a double-barreled syringe removably mounted to the handle, the double-barreled syringe including a first cylinder and a second cylinder, each cylinder including a respective pressure intake port at a proximal end and a fluid discharge port at distal end;
    a regulator assembly operably connected to the applicator assembly for providing a source of pressure to the applicator assembly to eject a first component contained within the first cylinder and a source of pressure to the applicator assembly to eject a second component contained within the second cylinder; and
    an atomizing tip provided at a distal end of the handle and in fluid communication with the fluid discharge ports of the double-barreled syringe, the atomizing tip including a proximal end defining a substantially hollow chamber configured to mix the first component and the second component, and a distal end configured to apply a mixture of the first and second components to tissue,
    wherein the regulator assembly includes at least three independently controllable regulators, two of the regulators being in fluid communication with the respective pressure intake ports associated with each of the cylinders and one of the regulators being in fluid communication with a pressure intake port disposed on the applicator, each of the regulators configured to provide a distinct amount of pressurized gas to its respective intake ports.

16. The applicator device as recited in claim 15, wherein the third regulator provides air pressure to the atomizing tip.

17. The applicator device as recited in claim 1, further comprising a first fluid discharge tube disposed in fluid communication with the fluid discharge port of the first cylinder and a second fluid discharge tube disposed in fluid communication with the fluid discharge port of the second cylinder, wherein each of the first fluid discharge tube and the second fluid discharge tube extends distally beyond a proximal wall of the atomizing tip.

18. The applicator device as recited in claim 2, further comprising a first fluid discharge tube disposed in fluid communication with the fluid discharge port of the first cylinder and a second fluid discharge tube disposed in fluid communication with the fluid discharge port of the second cylinder, wherein each of the first fluid discharge tube and the second fluid discharge tube extends distally beyond a proximal wall of the atomizing tip, and wherein each of the first fluid discharge tube and the second fluid discharge tube extends distally beyond a distal end of the pressure bore.

19. The applicator device as recited in claim 18, wherein the distal end of the pressure bore is substantially flush with the proximal wall of the atomizing tip.

\* \* \* \* \*